United States Patent [19]

Guibert

[11] Patent Number: 4,461,299
[45] Date of Patent: Jul. 24, 1984

[54] SCANNING HYPERTHERMIA TECHNIQUE

[75] Inventor: Raul Guibert, Los Angeles, Calif.

[73] Assignee: Sunset Ltd., Los Angeles, Calif.

[21] Appl. No.: 313,313

[22] Filed: Oct. 20, 1981

Related U.S. Application Data

[63] Continuation-in-part of Ser. No. 274,504, Jun. 16, 1981, Pat. No. 4,398,535, which is a continuation-in-part of Ser. No. 97,787, Nov. 27, 1979, Pat. No. 4,307,286.

[51] Int. Cl.$^3$ .............................................. A61F 7/00
[52] U.S. Cl. .................................................... 128/399
[58] Field of Search ................................ 128/399–400, 128/402, 375, 68.1; 223/51; 38/14, 15, 16; 248/618, 621, 632–633; 4/535–537, 567–570, DIG. 7, 605–606; 604/282

[56] References Cited

U.S. PATENT DOCUMENTS

| | | | |
|---|---|---|---|
| 1,017,700 | 2/1912 | Strock | 4/567 |
| 1,682,903 | 9/1928 | Hadaway | 38/16 X |
| 2,290,378 | 7/1942 | Motto | 4/567 |
| 3,610,251 | 10/1971 | Sanderson | 4/536 |
| 4,010,498 | 3/1977 | Jablonski | 4/569 |
| 4,044,765 | 8/1977 | Kline | 604/282 |
| 4,398,535 | 8/1983 | Guibert | 128/399 |

Primary Examiner—C. Fred Rosenbaum
Assistant Examiner—Gene B. Kartchner
Attorney, Agent, or Firm—Michael Ebert

[57] ABSTRACT

A heat therapy technique by which heat is applied to a limited skin area of a patient to penetrate the tissue and produce hyperthermia in an internal region underlying this area without, however, causing undue discomfort to the patient or damaging surface tissue. Periodically sweeping across the skin area and normal thereto is a broad beam of heated air in a pulsatory air wave pattern whose relatively brief pulses flow at high velocity and are at a high temperature well above body temperature and whose static intervals between pulses are at a medium temperature somewhat above body temperature. As a consequence, the transfer of heat from the surface tissue toward the internal region which takes place during these intervals acts to reduce the temperature of the surface tissue and to prevent it from reaching an unacceptable level despite the high temperature of the high-velocity pulses applied thereto.

5 Claims, 10 Drawing Figures

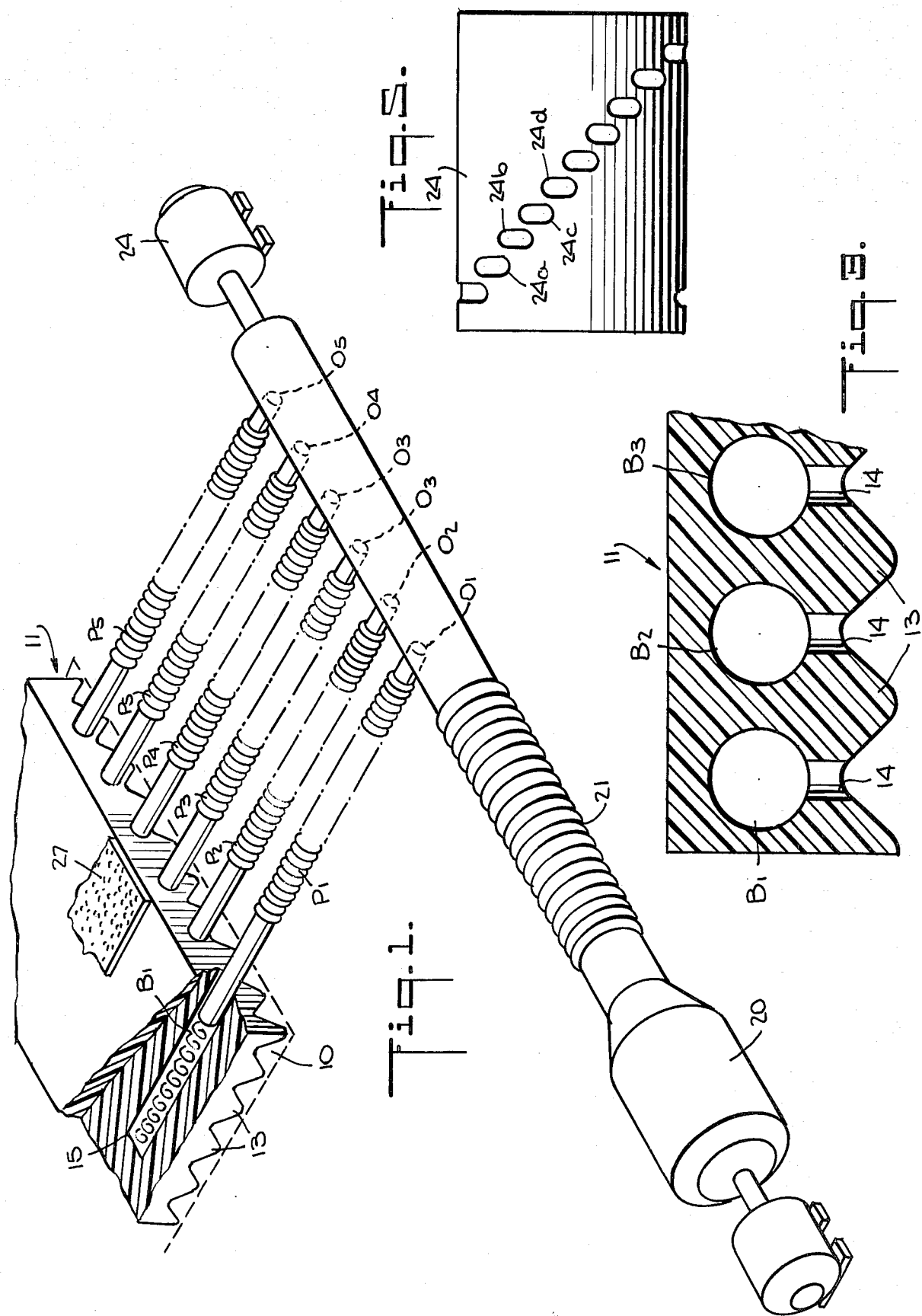

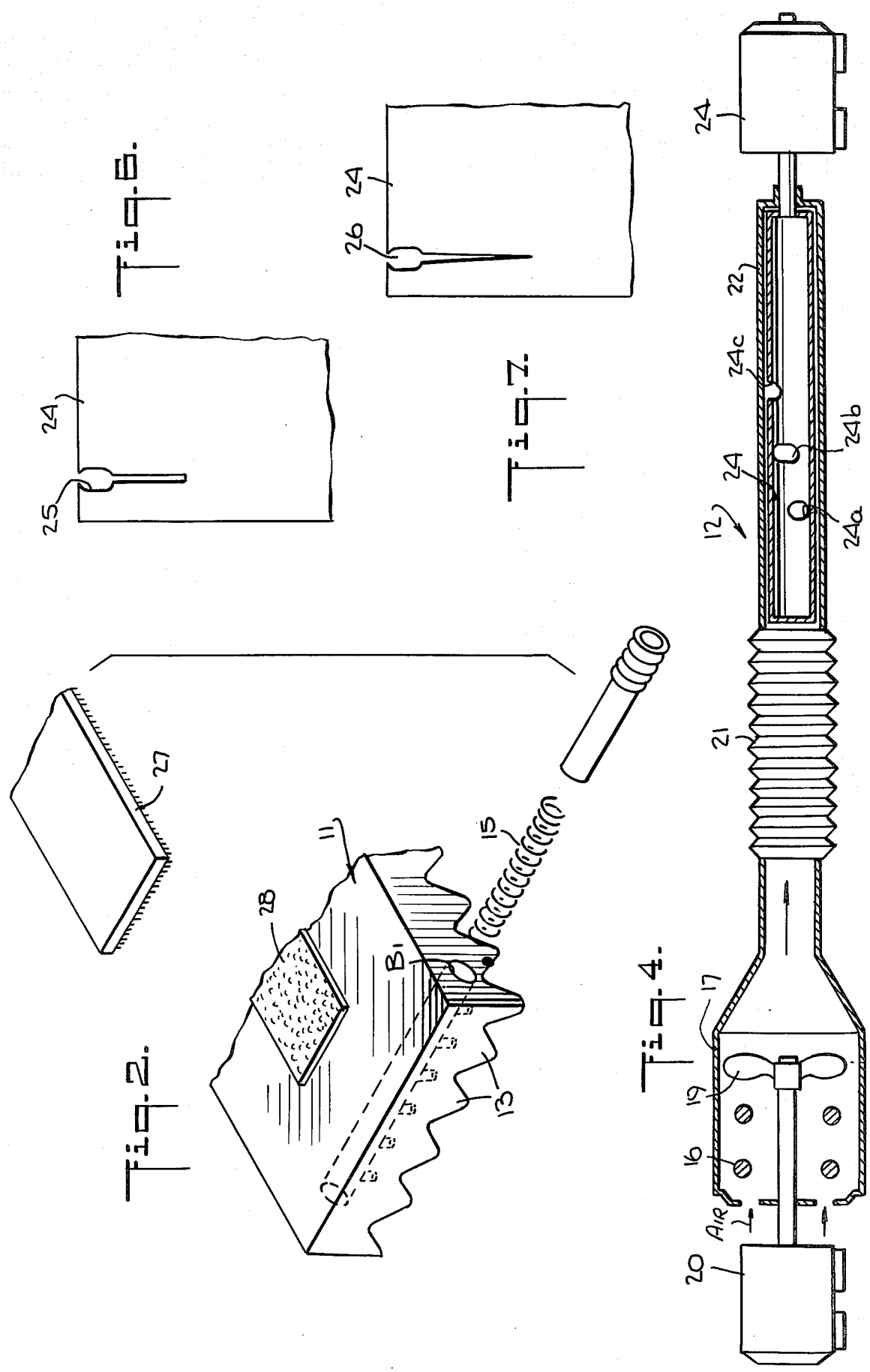

SCANNING HYPERTHERMIA TECHNIQUE

RELATED APPLICATION

This application is a continuation-in-part of my co-pending application Ser. No. 274,504, filed June 16, 1981, now U.S. Pat. No. 4,398,535, entitled "Hyperthermia Technique," which in turn is a continuation-in-part of my earlier application Ser. No. 097,787, filed Nov. 27, 1979, now U.S. Pat. No. 4,307,286 entitled "Pulsating Hot-Air Heat-Up System."

BACKGROUND OF INVENTION

This invention relates generally to techniques for the hyperthermia treatment of living tissue, and more particularly to devices for periodically sweeping a limited skin area of the body with a broad beam of heated high-velocity air pulses in a manner which acts to significantly raise the temperature of an internal region underlying the skin area without excessively heating surface tissue.

The interior of the human body has a normal temperature level which is usually said to be 98.6° F. But actually, in the course of each 24-hour period, the body temperature rises above and falls below this nominal value within a 1.8° F. range. Body temperature is determined by the relationship existing between the amount of heat internally generated, which depends on basal metabolism, and the amount of heat escaping from the body. Additional heat is produced as a result of muscular activity, this being dissipated by an increase in radiation, conduction or evaporation from the skin surface and by more rapid and deep breathing.

Thus the skin is the interface between the internally heated body and the atmosphere, and is in heat exchange relationship therewith. If the heat produced by a body surpasses heat losses therefrom, this gives rise to fever; but if heat losses exceed heat production, then the body temperature falls below the nominal value, resulting in shivering and hypothermia.

Medical practitioners since ancient times have known that the application of heat to the body is useful in the relief of muscle soreness and various aches and pains, as well as in the treatment of certain abnormalities. Thus the application of heat for the treatment of arthritis and other abnormal conditions is commonplace. Hot water bottles and electrical heating pads are in widespread use, not merely to provide warmth, but also to afford a degree of relief or therapy for various conditions. Heat is also used medically in the resolution of infected areas.

While the present invention is generally applicable to all abnormal conditions which can be benefited by the application of heat to the surface of the body, it will now be considered in the context of malignant tumor treatment. It is recognized that by heating tumors to a higher temperature than the surrounding tissue, the tumor may be caused to shrink and disappear. As noted in *The New York Times* of Apr. 14, 1981 (section C2) in an article on modern approaches to cancer treatment, the effectiveness of heat therapy is based on the fact that cancers have poor circulation and a reduced ability to dissipate heat. "Thus a temperature of more than 113 degrees Fahrenheit could destroy cancer cells while sparing normal tissue."

Patients with tumors in their arms and legs have been treated by a perfusion therethrough of hot blood, and tumors in bladders have been treated by flushing the organ with hot fluid. It has also been known to immerse patients in hot wax, and in some cases, medical practitioners have gone so far as to elevate the body temperature of patients by infecting them with malaria.

These known hyperthermia techniques, as well as those based on the use of microwave, high-frequency radiation and thermoelectric techniques are described in some detail in the patents to Sterzer, U.S. Pat. No. 4,190,053; Gordon, U.S. Pat. No. 4,106,488; Whalley, U.S. Pat. No. 4,121,592; Doss, U.S. Pat. No. 4,016,886; Bender, U.S. Pat. No. 4,186,294, and Ulrich, U.S Pat. No. 3,618,590.

Difficulty has heretofore been experienced in applying heat to a patient which is electrically or otherwise generated. When transferring heat through living tissue to a site underlying the skin, if the heat applied to the skin surface is within a tolerable temperature range, then not enough heat energy is transferred to the site to afford beneficial effects. When, however, the skin temperature of the applied heat is such as to bring out an adequate heat transfer to the internal site, when the skin temperature is usually above an acceptable level, and this may result in extreme discomfort to the patient and even to the burning of surface tissue. The same problem is encountered when using high-frequency radio heating; for, as pointed out in the above-identified Whalley patent, in many cases such treatment results in damage to the skin.

In my above-identified co-pending application Ser. No. 097,787, now U.S. Pat. No. 4,307,286 apparatus is disclosed whereby cold, pre-cooked packaged meals may be rapidly heated to a service temperature level without causing destructive re-cooking of the meals. To this end, applied to the package is a stream of heated air in a pulsatory thermal wave pattern whose pulses are at a temperature well above the service temperature level and whose intervals between pulses are at a lower temperature. As a result of this thermal wave pattern, heat is transferred from the surface of the food body to the interior thereof during the lower temperature intervals, thereby preventing the surface temperature from rising above the service temperature level, despite the fact that it is subjected to high temperature pulses.

In my above-identified copending application Ser. No. 274,504, now U.S. Pat. No. 4,398,535 this pulsatory thermal wave pattern is exploited to carry out heat therapy on patients without injury to surface tissue. In this patent application, use is made of a flexible foam pad applicator having an array of openings therein from which the hot air pulses are simultaneously projected against the skin area where a relatively large skin area is subjected to such hot air pulses. This may result in discomfort to the patient being treated.

While the present invention will be described mainly in connection with therapy produced by hyperthermia, the same principles are applicable to hypothermia treatment, in which therapeutic effects are produced by cooling an internal body site.

SUMMARY OF INVENTION

In view of the foregoing, the main object of this invention is to provide an apparatus which makes effective high temperature heat therapy feasible without inflicting injury to the surface tissue in the area where the heat is applied and without causing undue discomfort to the patient.

It must be borne in mind that when heat is applied to a skin area at a temperature which is significantly greater than body temperature, some unavoidable degree of discomfort will be experienced, particularly if the area is relatively large. The concern of the present invention is to keep such discomfort within a tolerable range and to avoid any damage to surface tissue.

More particularly, an object of this invention is to provide in a hyperthermia system, an applicator which is adapted to periodically sweep the skin area with a broad beam of heated air which is normal to the skin area and is in a pulsatory wave pattern to effect heat transfer to an internal region underlying this area to cause the temperature of the region to rise to a level appropriate to hyperthermia treatment without giving rise to an excessive temperature damaging to the surface tissue.

Yet another object of this invention is to provide a hyperthermia system which includes an applicator in the form of a flexible heating pad which is adapted to conform to a body area to be heated, said applicator having an array of parallel channels therein which are in the course of each operating cycle sequentially supplied with high-velocity hot air pulses which are projected toward the skin area of the patient being treated.

Also an object of the invention is to provide an efficient and reliable heat therapy instrument which is easy and safe to operate and which may be manufactured at relatively low cost.

Briefly stated, these objects are attained in a heat therapy technique by which heat is applied to a limited skin area of a patient to penetrate the tissue to produce hyperthermia in an internal region underlying this area without, however, causing undue discomfort to the patient or damaging surface tissue. Periodically sweeping across the skin area is heated air in a pulsatory air wave pattern whose relatively brief pulses flow at high velocity and are at a high temperature well above body temperature and whose static intervals between pulses are at a medium temperature, whereby the skin area is effectively divided into a series of sub-areas, only one sub-area at a time being subjected to high temperature pulses to minimize discomfort to the patient.

As a consequence, the transfer of heat from the surface tissue toward the internal region which takes place during the intervals acts to reduce the temperature of the surface tissue and to prevent it from reaching an unacceptable level despite the high temperature of the high-velocity pulses applied thereto.

OUTLINE OF DRAWINGS

For a better understanding of the invention as well as other objects and further features thereof, reference is made to the following detailed description to be read in conjunction with the accompanying drawings, wherein:

FIG. 1 illustrates, in perspective, a first preferred embodiment of a heat therapy system in accordance with the invention;

FIG. 2 shows, in perspective, the relationship between one manifold in the applicator of the system and the air supply pipe therefor;

FIG. 3 is a section taken through the applicator pad;

FIG. 4 is a section taken through the hot air modulator included in the system, the section being taken in the plane indicated by line 4—4 in FIG. 1;

FIG. 5 is a rectangular development of the hole pattern in the inner cylinder of the modulator;

FIG. 6 shows an alternative hold pattern;

FIG. 7 shows still another hole pattern;

DESCRIPTION OF INVENTION

First Embodiment

Figure 8:
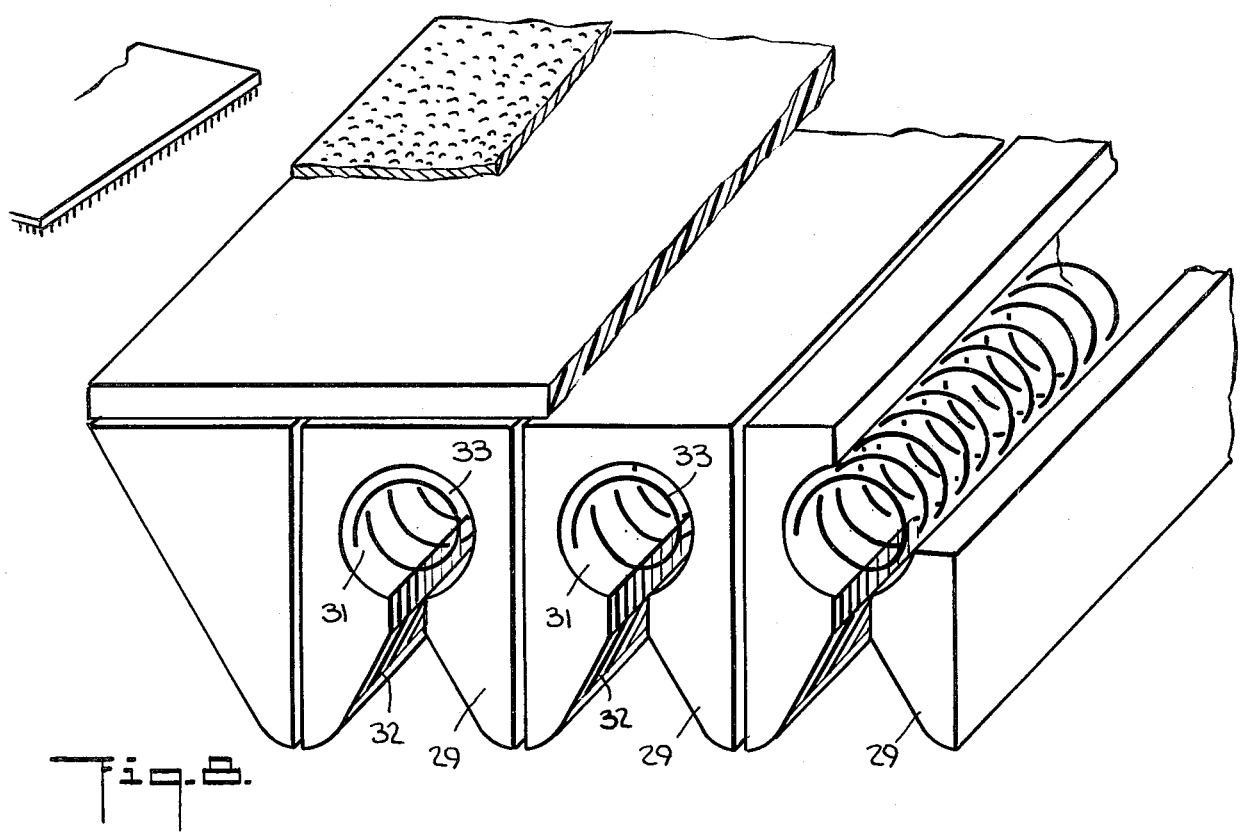
FIG. 8 is a perspective showing of a second embodiment of a system in accordance with the invention.

Referring now to FIGS. 1 to 4, there is shown a scanning heat therapy system for applying pulses of hot air to the skin surface of a patient in an area 10 in order to subject a tumor underlying this area to hyperthermia treatment.

The system includes an applicator, generally designated by numeral 11, to which is supplied pulses of hot air by a hot-air modulator 12. Applicator 11 is constituted by a rectangular pad preferably formed of synthetic plastic foam material, such as polyurethane, the front face of the pad being molded to define an array of projecting flexible fingers 13 which engage the skin area.

Formed in pad 11 along parallel transverse lines are bores $B_1$ to $B_6$. Each bore communicates with a row of nozzles 14, whereby the bore, in combination with the nozzles, functions as a manifold to project air into the troughs between the fingers. The pad is flexible; hence to retain the shape of the bores even when the pad is sharply curved, a helical coil 15 is inserted in each bore.

Modulator 12 is coupled to the bores by a group of flexible pipes $P_1$, $P_2$, $P_3$, etc.. whose rigid outlets are inserted in the respective bores. Modulator 12, as best seen in FIG. 4, includes a heat source constituted by electrical heater elements 16 disposed within a cylindrical casing 17 having an air inlet at one end, air being drawn into the casing by a propeller 19 operated by an external motor 20. The other end of the casing is coupled by a flexible tube 21 to an outer cylinder 22. Received within outer cylinder 22 is an inner cylinder 24 rotated by an external motor 23 and functioning as a valve or modulator. The inlets of pipes $P_1$ to $P_6$ are respectively coupled to a row of spaced ports or openings $O_1$ to $O_6$ along the outer cylinder.

Inner cylinder 24 is provided with holes 24a, 24b, 24c, etc., placed at circumferential positions in alignment with the inlet ports to pipes $P_1$ to $P_6$. The holes are angularly displaced so that at one angular position of inner cylinder 24, hole 24a is in registration with the inlet port to pipe $P_1$; at a second angular position, hole 24b is in registration with the inlet port to pipe $P_2$, and so on. Thus in the course of each full rotation of inner cylinder 24, hot air blow at high velocity into inner cylinder 24 is projected in sequence through pipes $P_1$ to $P_7$, and from these pipes into manifold Consequently, each pipe feeds a pulse of hot air into its associated manifold, only one manifold being active at a time. In operation, the air projected from manifold bore $B_1$ is directed onto the first sub-division of skin area 10, the hot air from manifold $B_2$ is directed onto the second sub-division of the skin area, and so on, until the entire area is scanned. The beam is normal to the skin.

In effect, therefore, from each manifold there is emitted a broad beam of hot air pulses which are directed onto a particular sub-division of the total skin area, this beam sweeping from sub-division to sub-division in the course of a full rotation. While six manifolds have been shown in applicator 11 opening in conjunction with six pipes and a modulator inner cylinder having six holes, this is by way of illustration only, and in practice a greater or smaller number may be used.

And while the inner cylinder holes shown in FIGS. 4 and 5 have an oblong form, in practice the holes may have different formations, as shown by hole in FIG. 6, where the oblong hole 25 has a rectangular tail, and in FIG. 7, where hole 26 has a triangular tail to avoid an abrupt no-flow interval after the inner cylinder brings the next hole in the series in registration with the next inlet pipe.

In practice, the applicator pad may be strapped onto the body of a patient at an appropriate site, use being made for this purpose of a strap 27 having a male Velcro component on its underside which engages a female Velcro component 28 attached to the surface of the pad.

In order to render the system also useful for hypothermia, element 16 may be of the thermoelectric type capable of selectively providing either a reduced temperature or an elevated temperature. Such thermoelectric elements make use of dissimilar metals and replace the mechanics of conventional refrigeration when operating in the cold mode. Thus when the system is operative in the hyperthermia mode, air drawn into casing 17 is heated and blown at high velocity into inner cylinder 24; and when the system is operative in the hypothermia mode, the air drawn into the casing is cooled and blown at high velocity into the inner cylinder to produce pulses of cold air.

Operation

Normal body temperature is 98.6° F. The pulsatory thermal wave pattern through each manifold is constituted by periodic pulses at a high temperature of, say, 150° F. and higher, and by no-flow or static intervals between pulses at a medium temperature somewhat above body temperature, such as 110.0° to 120° F. Because the high temperature air flows over the skin area at high velocity during the pulses, this forced convection results in a rapid heat exchange. And while the small volume of almost static air is confined between the applicator and the skin area during the static intervals has a very low thermal capacity and a low-heat transfer coefficient, its temperature, because of residual heat in the applicator, is somewhat above skin temperature. This prevents the release of heat from the body to the outside. The chosen value of the pulse temperature depends, of course, on the desired temperature level to be imparted to the tumor or whatever other region is to be treated.

The rate of pulsing is a crucial aspect of the invention, for the body region containing the tumor is formed of living tissue having relatively poor heat conductivity and is composed effectively of a succession of layers, beginning with the surface or skin layer and going through intermediate layers, etc., into the tumor. The tumor can be heated to a hyperthermia level above body temperature, say, to 115° F. and above, only by transmitting heat through the successive layers of poor thermal conductivity.

As noted in the article "Heat Therapy for Cancer" in *Discover*, June 1981, published by Time, Inc., because the circulation in tumors is poor, the blood moves sluggishly therein and does not carry away heat as rapidly as it does in ordinary tissue. When a tumor is to be heated to a lethal temperature of over 110° F., the heat imparted to the tumor is retained, whereas the tissue in the region between the tumor and skin then is subjected to a safe, lower temperature because of blood circulation. Tumor cells are apparently more sensitive to heat than normal cells and seem to have a higher metabolism; hence tumor cells are more easily overstressed by heat. While the question of whether cancerous cells have a greater sensitivity than normal cells remains controversial, there is little argument about the lethal effect of heat on tumors.

The outer layer is initially at 98.6° F. Assuming that each high temperature pulse period lasts 3 seconds followed by a five-second lower temperature interval, and that the first 150° F. pulse flowing past the skin area at high velocity for three seconds acts to raise the temperature of the outer layer to 104° F., then during the 110° F. interval which follows, heat from the outer layer will be transferred inwardly to a first intermediate layer which is thereby raised in temperature to, say, 100° F., with a resultant reduction in the temperature of the outer layer so, say, 102° F.

Thus the interval between the hot air pulses represents a relaxation period during which heat transfer takes place from the outside in, but not from the inside out; for the temperature outside the skin is always above the body temperature. When the outer layer, now at 102° F., is again subjected to the next hot air high velocity pulse at 150° F., this will raise the temperature of the outer layer another notch, and the temperature of this layer will again be somewhat reduced during the interval which follows when heat is transferred from the outer layer to the first intermediate layer.

It is important to bear in mind that a small volume of almost static air has a low thermal capacity and a low heat transfer coefficient. Because of the high velocity of the pulses, a large volume of air is brought into heat exchange relationship with the skin during the pulse period to effect heat transfer; whereas in the interval, it is only a small volume of air.

Similar heat transfer actions take place concurrently between the second and third intermediate layers and between the third and fourth intermediate layers, and so on, toward the tumor region, very much in the fashion of an electronic cascade counter in which when an input signal (heat pulse) is received, the state of each stage (layer) in the cascade is advanced in an ordered sequence.

Thus the intervals between hot air pulses applied to the surface layer of the body allows time for transfer of heat to take place from layer to layer; and because the outer layer is permitted to cool down during these intervals, the temperature of the outer layer is never permitted to rise to an excessive level, even when the tumor is heated to an effective hyperthermia temperature of about 115° F. And while the tissue between the tumor and the skin is also caused to rise in temperature, the cooling effect of the circulatory system prevents this tissue from being overheated.

In the present arrangement, at any one time, the hot air pulses are applied to a limited sub-division of the total skin area 10, the applicator scanning this area to cause hot air pulses to sweep sequentially across the successive sub-divisions. As a consequence, the sensation of heat is much less pronounced than if the entire air is subjected to hot air pulses, yet the heat transfer from the skin to the internal tumor occurs in essentially the same manner as in my prior application.

Second Embodiment

Figure 9:
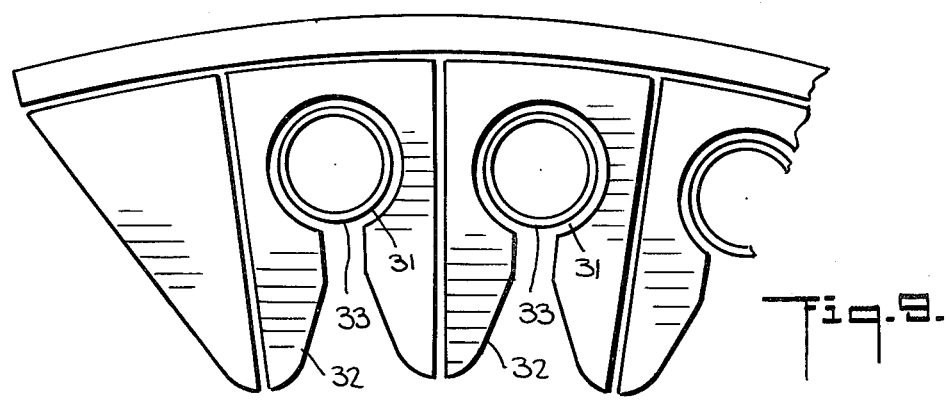
FIG. 9 is a section taken through the applicator shown in FIG. 8.
Figure 10:
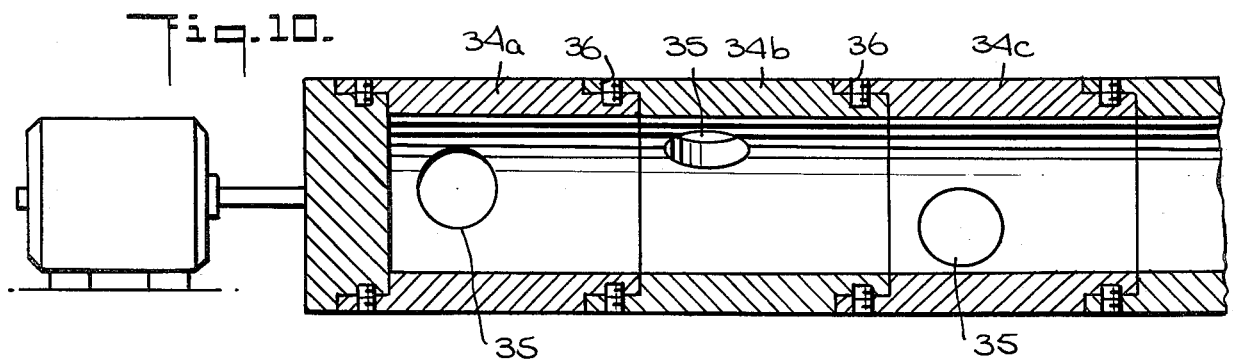
FIG. 10 is a section taken through an alternative form of modulator.

In the system shown in FIGS. 8, 9 and 10, the applicator is constituted by several extruded units 29 of silicone foam rubber or similar extrudable material which are linked together by a flexible top sheet. Each extrusion has a bore 31 formed therein which communicates with a diverging channel 32 extending the full length of the bore. A helical coil 33 inserted in the bore prevents its collapse when the applicator pad is flexed, as shown in FIG. 9.

Thus instead of the hot air being projected through a row of nozzles coupled to the bore as in FIG. 2, the hot air is emitted along the full length of the channel to provide a broad band of hot air for each sub-division of the skin area engaged by the applicator.

In the hot air modulator shown in FIG. 10, the inner cylinder, instead of being composed of a single tube as in FIG. 4, is made up of a series of interfitting ring sections 34a, 34b, 34c, etc., each having a hole 35 therein, the relative angular positions of the holes being adjustable by means of set screws 36. With this arrangement, one may set up as many sections as there are extruded units 29 in the applicator. This makes it possible to tailor the number of units in the applicator to particular requirements, and to set up the modulator accordingly.

While there have been shown and described preferred embodiments of a scanning hyperthermia technique in accordance with the invention, it will be appreciated that many changes and modifications may be made therein without, however, departing from the essential spirit thereof. Thus instead of emitting pulses of air from uninterrupted channels from the full length of the channels as shown in FIGS. 8 to 10, the channels may have plastic inserts therein provided with a series of orifices to produce a row of air jets. In practice, before the applicator is put to use, the skin area to be treated is preferably coated with Vaseline or other coating resistant to the temperatures involved, which acts to close the skin pores to prevent evaporative cooling.

I claim:

1. A scanning thermal therapy system for a living organism having a normal body temperature, the system serving to raise the temperature of a region underlying an area of body skin to a hyperthermia level having beneficial effects, said system comprising:
    A. an applicator adapted to be placed above said skin area and including a series of bores, each having an outlet for projecting hot air onto a related sub-division of the skin area; and
    B. cyclical means to supply hot air at high velocity to each of said bores sequentially in the course of each operating cycle, whereby each sub-division is subjected by its associated outlet to a high-velocity stream of periodic hot air pulses separated by relatively static intervals to produce a pulsatory wave, said pulses having a high temperature level well above said normal temperature, the static intervals between the pulses having a medium temperature level somewhat above said normal temperature, the heat produced by said pulsatory wave penetrating the skin to cause the region thereunder to rise in temperature to said hyperthermia level without injury to surface tissue, heat transfer inwardly from the surface layer of the tissue taking place during said intervals to cause a reduction in the temperature of the surface layer preventing excessive heating thereof.

2. A system as set forth in claim 1, wherein said high temperature level is about 150° F.

3. A system as set forth in claim 1, wherein said hyperthermia level is about 115° F.

4. A system as set forth in claim 1, wherein said hot air supply means includes an inner cylinder rotating within an outer cylinder having a row of ports therein, each of which is coupled to a respective outlet of the applicator, the inner cylinder having angularly displaced holes therein which register in sequence with said ports in the course of each rotation, and means to feed hot air at high velocity into the inner cylinder.

5. A system as set forth in claim 4, wherein said inner cylinder is formed by a series of interfitting sections.

* * * * *